United States Patent [19]
Devanathan

[11] Patent Number: 6,132,209
[45] Date of Patent: Oct. 17, 2000

[54] ORTHODONTIC WIRE

[75] Inventor: Thrumal Devanathan, Warsaw, Ind.

[73] Assignee: TP Orthodontics, Inc., Westville, Ind.

[21] Appl. No.: 09/291,691

[22] Filed: Apr. 13, 1999

[51] Int. Cl.[7] .................................................. A61C 3/00
[52] U.S. Cl. .................................................. 433/20
[58] Field of Search ......................................... 433/20, 24

[56] References Cited

U.S. PATENT DOCUMENTS

| | | | |
|---|---|---|---|
| 4,037,324 | 7/1977 | Andreasen | 433/24 |
| 4,197,643 | 4/1980 | Burnstone et al. | 433/20 |
| 4,717,341 | 1/1988 | Goldberg et al. | 433/9 |
| 5,017,133 | 5/1991 | Miura | 433/20 |
| 5,044,947 | 9/1991 | Sachdeva et al. | 433/20 |
| 5,433,603 | 7/1995 | Mollenhauer et al. | 433/24 |
| 5,573,401 | 11/1996 | Davidson et al. | 433/201.1 |
| 5,683,245 | 11/1997 | Sachdeva et al. | 433/20 |
| 5,692,899 | 12/1997 | Takahashi et al. | 433/20 |
| 5,882,193 | 3/1999 | Wool | 433/20 |

OTHER PUBLICATIONS

Nikolai, Robert J., Orthodontic Wire: A Continuing Evolution, Seminars in Orthodontics, vol. 3, No. 3, Sep., 1997, pp. 157–165.

*Primary Examiner*—John J. Wilson
*Assistant Examiner*—Melba Bumgarner
*Attorney, Agent, or Firm*—Lloyd L. Zickert

[57] ABSTRACT

A wire for orthodontically treating patients in the application of corrective forces to teeth made of a titanium-aluminum-vanadium alloy providing a substantially constant significantly lower force than stainless steel wire.

10 Claims, No Drawings

ORTHODONTIC WIRE

This invention relates in general to an orthodontic wire for providing movement forces to teeth that are greater than beta titanium wire and lower than stainless steel wire, and more particularly to an orthodontic wire having a significantly constant lower force component than that of stainless steel and a slightly higher force component than that of beta titanium, while having about half the stiffness of a comparable stainless steel wire.

BACKGROUND OF THE INVENTION

Heretofore, it has been well known to have orthodontic wires for delivering force components to teeth made of 18-8 stainless steel wire. Such wire has a modulus of elasticity of around $30\times10^6$ psi. It has also been known to provide orthodontic wire of a cobalt chromium alloy which likewise has a modulus of elasticity at least as high and sometimes higher than stainless steel wire.

With the advent of lighter force requirements being the trend in orthodontic treatment, various nickel titanium wires have been developed and defined as having a beta titanium alloy such as disclosed in U.S. Pat. No. 4,197,643. These beta titanium wires have a much lower elastic modulus of about $10\times10^6$ psi. Accordingly, such wires deliver a substantially lower force to the teeth when used in conjunction with orthodontic appliances.

There have also been developed orthodontic wires considered to be super elastic and of a nickel titanium alloy and having even a substantially lower elastic modulus than beta titanium wire. An example of a superelastic wire is disclosed in U.S. Pat. No. 5,044,947. For example, such wires have a modulus of elasticity of around 4 to $5\times10^6$ psi. These wires may also be temperature sensitive for returning to a desired shape when placed in the mouth.

It is desirable where lower force mechanics are used for orthodontic treatment to utilize a wire having a lower modulus of elasticity to provide a constant moderately low level force than that obtainable with stainless steel wires. Thus, the beta titanium wires have been generally utilized where a lower force is desired. One disadvantage of such wire is that it is relatively high in cost compared to the stainless steel wires. Moreover, the formability of a beta titanium wire is still not as good as wires having higher force components, while it is better than nickel titanium wires.

SUMMARY OF THE INVENTION

The present invention is in an orthodontic wire having better formability than beta titanium wires, while delivering a higher force and maintaining a stiffness that is about half that of stainless steel wire but which cost much less. Moreover, the wire of the present invention is capable of delivering a higher constant force than a beta titanium wire.

The wire of the present invention is made of a titanium-aluminum-vanadium alloy which consists of about 6 percent aluminum by weight, 4 percent vanadium by weight, and essentially the remainder in titanium. The wire of the invention has the ability to deliver approximately a 30 percent higher constant force than beta titanium wires, while at the same time delivering a significantly constant lower force than stainless steel wires.

The wire of the present invention, being made of a titanium-6 aluminum-4 vanadium alloy, has a proven biocompatibility in that this alloy has been used extensively for years in implantable appliances for hip and knee joints, as well as other human joints. As a surgical implant material, it has been shown to have an acceptable level of biocompatibility and has been approved by national and international and non-governmental organizations.

DESCRIPTION OF THE INVENTION

The present invention is in an orthodontic wire such as an archwire used for effective movement of teeth when orthodontically treating a patient when the archwire coacts with appliances mounted on the teeth to impart force-correcting movements to the teeth. When used as an archwire, it may be made in round or rectangular cross sections depending upon the use being made during orthodontic treatment. Further, the wire of the invention can be used in any suitable uprighting or rotating springs or wherever there is a need in the mouth to impart a substantially constant low level force for correcting teeth orientation and location.

The wire of the invention is made of a titanium-aluminum-vanadium based alloy wherein it comprises by weight about 6 percent aluminum, 4 percent vanadium, and the balance in titanium. The modulus of elasticity of wire from this alloy will be in the range of 14 to $17\times10^6$ psi and therefore about half that of stainless steel which is in the range of 25 to $30\times10^6$ psi. Moreover, the modulus of elasticity will be higher than nickel titanium wire which would be about $5\times10^6$ psi and beta titanium wire which would be about $10.5\times10^6$ psi. Thus, the modulus of elasticity of the wire of the present invention would be greater than nickel or beta titanium wire and significantly less than stainless steel wire.

Moreover, the wire of the present invention would be of a wrought annealed titanium-6 aluminum-4 vanadium ELI (extra low interstitial) alloy of the type used in the current manufacture of surgical implants.

The following examples of TI-6Al-4V ELI wires are provided as to their chemical composition and properties.

EXAMPLE I

| Chemical Composition (percent) | |
|---|---|
| C | .02 |
| Fe | .10 |
| Al | 5.78 |
| N | .010 |
| H | .0091 |
| | (average final hydrogen analysis) |
| O | .06 |
| V | 3.8 |
| Ti | BAL |

| Properties | |
|---|---|
| DIA. (") | .016 |
| TENSILE STRENGTH (p.s.i.) | 186,000 |
| BREAKING LOAD (lbs.) | 37.7 |
| ELONGATION (%) | 3.3 |
| GAGE LENGTH (") | 10 |

EXAMPLE II

| Chemical Composition (percent) | |
|---|---|
| C | .02 |
| Fe | .10 |
| Al | 5.78 |

-continued

| | |
|---|---|
| N | .010 |
| H | .0053 |
| | (average final hydrogen analysis) |
| O | .06 |
| V | 3.8 |
| Ti | BAL |

| Properties | |
|---|---|
| DIA. (") | .018 |
| TENSILE STRENGTH (p.s.i.) | 184,000 |
| BREAKING LOAD (lbs.) | 47.1 |
| ELONGATION (%) | 2.5 |
| GAGE LENGTH (") | 10 |

EXAMPLE III

| Chemical Composition (percent) | |
|---|---|
| C | .012 |
| Mn | .01 |
| Si | .01 |
| Cr | .01 |
| Mo | .01 |
| Fe | .09 |
| Al | 5.82 |
| N | .015 |
| Cu | .01 |
| H | .0033 |
| | (average final hydrogen analysis) |
| O | .012 |
| V | 3.86 |
| Ti | BAL |

| Properties | |
|---|---|
| DIA. (") | .032 |
| TENSILE STRENGTH (p.s.i.) | 160,000 |
| BREAKING LOAD (lbs.) | 131.6 |
| ELONGATION (%) | 11 |
| GAGE LENGTH (") | 10 |

EXAMPLE IV

| Chemical Composition (percent) | |
|---|---|
| C | .012 |
| Mn | .01 |
| Si | .01 |
| Cr | .01 |
| Mo | .01 |
| Fe | .09 |
| Al | 5.82 |
| N | .015 |
| Cu | .01 |
| H | .0024 |
| | (average final hydrogen analysis) |
| O | .12 |
| V | 3.86 |
| Ti | BAL |

| Properties | |
|---|---|
| DIA. (") | .036 |
| TENSILE STRENGTH (p.s.i.) | 155,000 |
| BREAKING LOAD (lbs.) | 159.1 |
| ELONGATION (%) | 10 |
| GAGE LENGTH (") | 10 |

The above examples relate to wires having round cross-sectional shapes but the shape of the wire of this invention is not limited to being round. It will be appreciated that a square or rectangular cross-sectional shape can be used particularly for archwires. However, it will be appreciated that normally a round wire will be used for making springs.

In view of the foregoing, it may be appreciated that the wire of the present invention is highly useful to produce desirable force components in orthodontic treatment of patients with a relatively low substantially constant moderate force that may be slightly higher than what is produced by beta titanium wires but at a much lower cost.

It will be understood that modifications and variations may be effected without departing from the scope of the novel concepts of the present invention, but it is understood that this application is to be limited only by the scope of the appended claims.

The invention is hereby claimed as follows:

1. A constant-force wire for orthodontic treatment comprising:

an orthodontic wire made of Ti—Al—V based wrought annealed, extra low interstitial alloy.

2. The wire according to claim 1, wherein the Ti—Al—V based alloy comprises about 6 percent Al, 4 percent V and the balance Ti.

3. The wire according to claim 1, wherein the wire is about 0.016 inch in diameter.

4. The wire according to claim 1, wherein the wire is about 0.018 inch in diameter.

5. The wire according to claim 1, wherein the alloy contains about 6 percent by weight aluminum, about 4 percent by weight vanadium, and the balance substantially titanium.

6. The wire according to claim 1, wherein the alloy has a modulus of elasticity in the range of $14-17 \times 10^6$ psi.

7. The wire according to claim 1, wherein the alloy has a modulus of elasticity greater than beta titanium wire and significantly less than stainless steel wire.

8. The orthodontic wire of claim 1, wherein the alloy has a modulus of elasticity between that of a beta-titanium alloy and a stainless steel alloy or a cobalt chromium alloy.

9. The orthodontic wire of claim 1, wherein the alloy has a modulus of elasticity of about $16 \times 10^6$ psi.

10. In an orthodontic appliance having a force-imparting wire for applying corrective forces to a tooth, said wire comprising a wrought annealed extra low interstitial alloy based on aluminum, vanadium and titanium, wherein the wire consists essentially of about 6 percent aluminum by weight, 4 percent vanadium by weight, and the remainder in titanium, and having a modulus of elasticity greater than beta titanium alloy wire and less than stainless steel alloy wire.

* * * * *